United States Patent [19]

Johnson et al.

[11] Patent Number: 5,145,845
[45] Date of Patent: Sep. 8, 1992

[54] SUBSTITUTED 2-CARBOXYLINDOLES HAVING PHARMACEUTICAL ACTIVITY

[75] Inventors: Graham Johnson, Ann Arbor; Thomas C. Malone, Canton; Po-Wai Yuen, Ann Arbor, all of Mich.

[73] Assignee: Warner-Lambert Co., Morris Plains, N.J.

[21] Appl. No.: 699,875

[22] Filed: May 14, 1991

[51] Int. Cl.$^5$ .............. A61K 31/40; A61K 31/415; C07D 209/18; C07D 403/04
[52] U.S. Cl. .................. 514/80; 514/274; 514/392; 514/419; 544/316; 548/318; 548/414; 548/483; 548/492
[58] Field of Search ........... 548/483, 492, 318, 414; 514/419, 80, 274, 392; 544/316

[56] References Cited

U.S. PATENT DOCUMENTS

| | | | |
|---|---|---|---|
| 3,182,071 | 5/1965 | Shavel et al. | 548/492 |
| 3,364,224 | 1/1968 | Shavel et al. | 546/86 |
| 3,472,870 | 10/1969 | Larsen et al. | 548/504 |
| 3,574,737 | 4/1971 | Grigst et al. | 548/123 |
| 4,960,786 | 10/1990 | Salituro et al. | 514/419 |
| 4,980,368 | 12/1990 | Thielke et al. | 514/415 |

FOREIGN PATENT DOCUMENTS 0394905 10/1990 European Pat. Off. .
0396124 11/1990 European Pat. Off. .

OTHER PUBLICATIONS

Russo et al., *Farmaco, Ed. Sci.*, 43(5), pp. 409–420, 1988.
R. Schwarcz, et al., *The Lancet*, pp. 140–143 (1985).
Choi, *Neuron.* 1:623–634 (1988).
B. Meldrun, "Neurotoxins and Their Pharmacological Implications" edited by P. Jenner, Raven Press, New York pp. 34–53 (1987).
J. W. McDonald, et al., *Eur. J. Pharmacol.*, 140:359–361 (1987).
J. F. Church, et al., *Anesthesiology* 69:702–709 (1988).
R. Gill, et al, *J. Neurosci.* 7:3343–3349 (1987).
S. M. Rothman, et al., *Neurosci.*, vol. 21, No. 3, pp. 673–678 (1987).
Gray et al., *J. Med. Chem.*, vol. 34, No. 4, pp. 1283–1292 (1991).
M. P. Goldberg, et al., *Neurosci. Lett.* 80:11–15 (1987).
Leeson et al., *J. Med. Chem.*, vol. 34, No. 4, pp. 1243–1252 (1991).
J. A. Kemp, et al., *TIPS* 8:414–415 (1987).
R. Gill, et al., *J. Neurosci.* vol. 21, No. 3, pp. 847–855 (1988).
C. K. Park, et al., *Ann. Neurol.* 24 No. 4, pp. 543–551 (1988).
G. K. Steinberg, et al., *Stroke* 19:1112–1118 (1988).
Abstract No. 9, paper entitled "Novel Glycine Antagonists" presented Apr. 1991 at 201st Annual American Chemical Soc. Meeting.
PCT Gazette, Section 1, No. 9, WO91/04973, p. 3184 (1991).

*Primary Examiner*—Patricia L. Morris
*Attorney, Agent, or Firm*—Joan Thierstein

[57] ABSTRACT

The present invention relates to novel compounds, which are derivatives of ureas, thioureas, carbamates, sulfonylureas, sulfonamides, amides, and thioamides of 2-carboxyindoles as illustrated by the formula

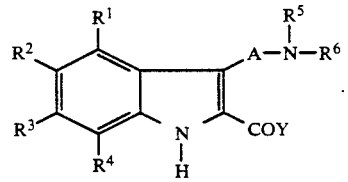

The invention also relates to methods for the preparation of the novel compounds, as well as to pharmaceutical compositions or methods of use for the novel compounds. More specifically, the compounds of the present invention are useful in the treatment of neurodegenerative disorders including cerebrovascular disorders as well as in the treatment of schizophrenia or epilepsy; and as analgesics and anxiolytics.

16 Claims, No Drawings

SUBSTITUTED 2-CARBOXYLINDOLES HAVING PHARMACEUTICAL ACTIVITY

BACKGROUND OF THE INVENTION

The present invention relates to novel compounds, which are derivatives of ureas, thioureas, carbamates, sulfonylureas, sulfonamides, amides, and thioamides of 2-carboxyindoles. The invention also relates to methods for the preparation of the novel compounds, as well as to pharmaceutical compositions or methods of use for the novel compounds. More specifically, the compounds of the present invention are useful in the treatment of neurodegenerative disorders including cerebrovascular disorders as well as in the treatment of schizophrenia or epilepsy; and as analgesics and anxiolytics.

Excessive excitation by neurotransmitters can cause the degeneration and death of neurons. It is believed that this neurodegeneration is in part mediated by the excitotoxic actions of the excitatory amino acids (EAA) glutamate and aspartate at N-methyl-D-aspartate (NMDA), α-amino-3-hydroxy-5-methyl-isoxazole propionic acid (AMPA), and kainate receptors. This excitotoxic action is responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery and cerebral trauma.

There are no specific therapies for these neurodegenerative diseases; however, compounds which act specifically as antagonists of EAA receptors and in particular the NMDA receptor complex, either competitively or noncompetitively, offer a novel therapeutic approach to these disorders: R. Schwarcz and B. Meldrum, *The Lancet* 140 (1985); B. Meldrum in "Neurotoxins and Their Pharmacological Implications" edited by P. Jenner, Raven Press, New York (1987); D. W. Choi, *Neuron* 1:623 (1988). Confirmation of the protective effects of noncompetitive NMDA antagonists in various pharmacological models of neurodegenerative disorders have appeared in the literature: J. W. McDonald, F. S. Silverstein, and M. V. Johnston, *Eur. J. Pharmacol.* 140:359 (1987); R. Gill, A. C. Foster, and G. N. Woodruff, *J. Neurosci.* 7:3343 (1987); S. M. Rothman, J. H. Thurston, R. E. Hauhart, G. D. Clark, and J. S. Soloman, *Neurosci.* 21:673 (1987); M. P. Goldbert, P-C. Pham, and D. W. Choi, *Neurosci. Lett.* 80:11 (1987); L. F. Copeland, P. A. Boxer, and F. W. Marcoux, *Soc. Neurosci. Abstr.* 14 (part 1):420 (1988); J. A. Kemp, A. C. Foster, R. Gill, and G. N. Woodruff, *TIPS* 8:414 (1987); R. Gill, A. C. Foster, and G. N. Woodruff *J. Neurosci.* 25:847 (1988); C. K. Park, D. G. Nehls, D. I. Graham, G. M. Teasdale, and J. M. McCulloch, *Ann. Neurol.* 24:543 (1988); G. K. Steinburg, C. P. George, R. DeLaPlaz, D. K. Shibata, and T. Gross, *Stroke* 19:1112 (1988); J. F. Church, S. Zeman, and D. Lodge, *Anesthesiology* 69:702 (1988).

U.S. Pat. No. 4,960,736 discloses certain 2-carboxy indole derivatives useful as excitatory (EAA) amino acid antagonists and EP Application Numbers 90107633.1 and 90108337.8 also disclose certain 2-carboxy indole derivatives for use to treat neurotoxic injury or neurodegenerative diseases known to be caused by or accelerated by certain EAAs found in the central nervous system (CNS).

U.S. Pat. No. 3,472,870 (Derwent Abstract No. 37,778), U.S. Pat. No. 3,364,224 (Abstract No. 30,396), teach sulphamidotryptamines and β-carbolines, respectively, differing by their failure to show the $R^1$, $R^2$, $R^3$, and $R^4$ substituents and amide linkage of the present invention. U.S. Pat. No. 3,182,071 (Derwent Abstract No. 16,591) discloses acylated indoles also differing in substituents and amide linkages.

U.S. Pat. No. 3,574,737 teaches iminocarbamic acid ester derivatives including a benzopyrrole(indole) substrate having urea-like substituents but without an amido linkage as a fungicide.

Additionally, U.S. application Ser. No. 07/670,860, filed Mar. 18, 1991, which is copending to the present application, teaches amides of indoles, thus differing from the present invention with amine-type substituents on indoles. Other references include 1) *J. Med. Chem.* 1991, Vol. 34, No. 4, pp. 1243+ and (2) *J. Med. Chem.* 1991, Vol. 34, No. 4, pp. 1283+. The first of these *J. Med. Chem.* disclosures includes a 2-carboxyindole which differs from the present invention by the lack of a 3-substituent. The second *J. Med. Chem.* disclosure features various indole dicarboxylate derivatives but, particularly, does not provide the 3-substituent of the present invention.

In Abstract No. 9 and paper entitled "Novel Glycine Antagonists", presented at the 201st Annual American Chemical Society Meeting at Atlanta, Ga., on Apr. 14–19, 1991, Medicinal Chemistry Section, teach a urea substituent on a substrate that is not an indole.

*Science,* 1989, Vol. 243, page 1611 describes selected 2 carboxyindoles which antagonize the strychnine insensitive glycine site of the NMDA receptor. The disclosed 2-carboxyindoles do not suggest the amide derivatives of the present invention.

PCT/DK90/00257 discloses indole derivatives having CNS activities differing in structure from the present invention by the substituents thereon.

However, although the present invention is also 2-substituted indoles, none of these references teaches the substituent represented by $ANR^5R^6$ in the present invention. The compounds of this application are 2-carboxyindoles and derivatives thereof having as substituents, for example, hydroxamide, amide, urea amide, ester amide, or sulphonamide.

SUMMARY OF THE INVENTION

The present invention provides compounds of the formula (I)

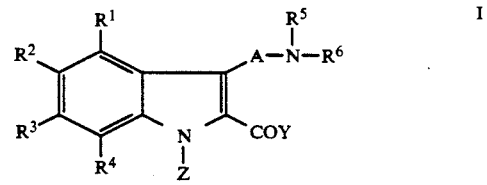

or tautomers or isomers thereof; or a pharmaceutically acceptable base or acid addition salt thereof; wherein (1) Y is (a) OH; (b) $OR_{30}$ wherein $R_{30}$ is lower alkyl, optionally substituted phenyl, or phenylalkyl wherein the alkyl is an alkylene of from one to four carbons and the phenyl is optionally substituted wherein the optional substituents on the phenyl are selected from one to three of lower alkyl, halogen, trifluoromethyl, nitro, amino, mono- or di-lower alkylamino, hydroxy, lower alkoxy, C(O)OH, or NHCOR$^5$ wherein R$^5$ is (i) lower alkyl, (ii) lower alkenyl, (iii) aryl, (iv) arylloweralkyl, (v) arylloweralkenyl, (vi) heteroaryl, or (vii) heteroarylloweraralkyl wherein the aryl is as defined below; (c) NR$_{40}$R$_{50}$ wherein R$_{40}$ and R$_{50}$ are independently hydrogen or lower alkyl; or (d) OCH$_2$OR$_{30}$ wherein R$_{30}$ is as defined above;

(2) Z is hydrogen or a pharmacologically labile protecting group;

(3) R$^1$, R$^2$, R$^3$, and R$^4$ are independently hydrogen, lower alkyl, halogen, trifluoromethyl, cyano, nitro, methylthio, lower alkenyl, lower alkynyl, SO$_2$NH$_2$, S(O)$_{1-2}$R wherein R is hydrogen or lower alkyl, OCF$_3$, or two of R$^1$, R$^2$, R$^3$, and R$^4$ can be taken together to form a carbocyclic ring of six carbons or can be taken together with one or more heteroatoms to form a heterocyclic ring wherein the heteroatom is selected from oxygen, sulfur, or nitrogen, and wherein the carbon on the carbocyclic ring is optionally further substituted by one of R$^1$, R$^2$, R$^3$, or R$^4$;

(4) A is —(CH$_2$)$_n$—, —(CH$_2$)$_q$CH=CH(CH$_2$)$_p$—,

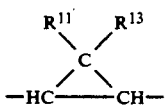

wherein R$^{11}$ and R$^{13}$ are independently as defined below and n is an integer of 0 through 4, q is an integer of 0 or 1 and p is an integer of 1 or 2;

(5) R$^5$ is hydrogen, alkyl of from one to twenty carbons or aryl;

(6) R$^6$ is (a) CONR$^8$R$^9$, (b) CSNR$^8$R$^9$, (c) COOR$^8$, (d) CSR$^8$, (e) S(O)$_{1-2}$R$^8$, (f) S(O)$_{1-2}$NR$^8$R$^9$, or (g) CONR$^8$S(O)$_{1-2}$R$^9$, wherein R$^8$ and R$^9$ are independently (i) hydrogen; (ii) alkyl of from one to twenty carbons, preferably one to twelve carbons, or alkenyl of from one to twenty carbons, preferably one to twelve carbons; (iii) cycloalkyl or cycloalkylloweralkyl; (iv) aryl which is phenyl unsubstituted or substituted by one to three of lower alkyl, halogen, trifluoromethyl, nitro, amino, mono- or di-lower alkylamino, hydroxy, lower alkoxy, C(O)OH, or NHCOR$^{10}$ wherein R$^{10}$ is lower alkyl, lower alkenyl, aryl, arylloweralkyl, arylloweralkenyl, heteroaryl, or heteroarylloweralkyl, NHSO$_2$R$^{10}$ wherein R$^{10}$ is as defined above, CN, CONR$^{10}$R$^{11}$ wherein R$^{10}$ is as defined above and R$^{11}$ is hydrogen or lower alkyl, preferably hydrogen, S(O)$_{0-2}$R$^{10}$ wherein R$^{10}$ is as defined herein; (v) arylloweralkyl; (vi) arylloweralkenyl; (vii) heterocycle; (viii) heteroaryl; (ix) (CH$_2$)$_q$R$^{12}$ wherein q is an integer of one to four and R$^{12}$ is (A) heterocycle, (B) heteroaryl, (C) SO$_3$R$^{13}$ wherein R$^{13}$ is hydrogen or lower alkyl (D) PO$_3$R$^{13}$, wherein R$^{13}$ is as defined above, (E) CO$_2$R$^{13}$ wherein R$^{13}$ is as defined above, or (F) NR$^{14}$R$^{15}$ wherein R$^{14}$ and R$^{15}$ are independently hydrogen or alkyl or R$^{14}$ and R$^{15}$ are taken together with N to form a heterocyclic or heteroaryl ring; or (x) amino acid residues; or (7) R$^5$ and R$^6$ are taken together with N which form

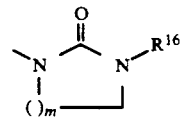

wherein m is an integer one or two and R$^{16}$ is lower alkyl, aryl, arylloweralkyl, heteroaryl, or heteroarylloweralkyl.

The present invention also includes a pharmaceutical composition comprising a therapeutically effective amount of a compound of Formula I together with a pharmaceutically acceptable carrier.

The present invention also includes a pharmaceutical composition for the use of treating cerebrovascular disorders, treating disorders responsive to the blockade of glutamic and aspartic acid receptors, for example, treating cerebral ischemia, cerebral infarction, cerebral vasospasm, hypoglycemia, cardiac arrest, status epilepticus, cerebral trauma, schizophrenia, epilepsy, neurodegenerative disorders, Alzheimer's disease, pain, anxiety, or Huntington's disease. Such a composition comprises an amount effective for treating each of such disorders, i.e., a therapeutically effective amount, together with a pharmaceutically acceptable carrier.

The present invention also includes a method of manufacturing a composition for or a method for treating cerebrovascular disorders which comprises administering to a patient in need thereof the above pharmaceutical composition in unit dosage form.

The present invention also includes a method of manufacturing a composition for or a method for treating disorders responsive to the blockade of one or both of glutamic and aspartic acid receptors comprising administering to a patient, including a human, in need thereof a therapeutically effective amount of the above composition.

The invention also includes a method of manufacturing a composition for or a method for treating cerebral ischemia, cerebral infarction, cerebral vasospasm, hypoglycemia, cardiac arrest, status epilepticus, cerebral trauma, schizophrenia, epilepsy, neurodegenerative disorders, Alzheimer,s disease, pain, anxiety, or Huntington's disease comprising administering to a patient in need thereof a therapeutically effective amount of the above composition.

The invention also includes a method of manufacturing a composition for or a method for treating stroke in patients in need thereof which comprises administering to a patient in need thereof a therapeutically effective amount of the above composition.

The invention further includes processes for the preparation of compounds of Formula I.

The invention still further includes novel intermediates useful in the processes.

1. Methyl 4,6 dichloro-3-[2-[[(phenylamino)carbonyl]amino]ethyl]-1H-indole-2-carboxylate;
2. Methyl 4,6 dichloro-3-[2-[[[(phenylmethyl)amino]-carbonyl]amino]ethyl]-1H-indole-2-carboxylate;
3. Methyl 4,6 dichloro 3-[2-[[[(3,5-dichlorophenyl)amino]carbonyl]amino]ethyl]-1H-indole -2-carboxylate;
4. Methyl 4,6 dichloro-3-[2-[[[(2-carboxylate;
5. Methyl 4,6 dichloro 3-[2-(2-oxo 3 phenyl-1-imidazolidinyl)ethyl]-1H-indole-2 carboxylate;
6. 4,6-Dichloro 3-[2 [[(phenylamino)carbonyl]amino]ethyl]-1H-indole-2-carboxylic acid;

7. 4,6-Dichloro-3-[2-[[[(phenylmethyl)amino]carbonyl]amino]ethyl]-1H-indole-2 carboxylic acid;
8. 4,6-Dichloro 3-[2-[[[(3,5-dichlorophenyl)amino]carbonyl]amino]ethyl]-1H-indole-2-carboxylic acid;
9. 4,6-Dichloro 3-[2-[[[(2-methylphenyl)amino]carbonyl]amino]ethyl]-1H-indole-2-carboxylic acid;
10. 4,6 Dichloro-3-[2-(2 oxo 3-phenyl 1-imidazolidinyl)ethyl]-1H-indole-2-carboxylic acid;
11. 4,6-Dichloro-3-[[(phenylamino)carbonyl]amino]-1H-indole-2 carboxylic acid;
12. 4,6-Dichloro-3 [[[(phenylamino)carbonyl]amino]methyl]-1H-indole 2 carboxylic acid;
13. 4,6 Dichloro 3-[3-[[(phenylamino)carbonyl]amino]propyl]-1H-indole-2-carboxylic acid;
14. 4,6 Dichloro 3-[3 (2-oxo-3-phenyl-1-imidazolidinyl)-propyl]-1H-indole-2-carboxylic acid;
15. 4,6-Dichloro-3-[(2-oxo-3 phenyl-1-imidazolidinyl)-methyl]-1H-indole 2-carboxylic acid;
16. 4,6-Dichloro-3-(2-oxo-3-phenyl 1-imidazolidinyl)-1H-indole-2-carboxylic acid;
17. 4,6-Dichloro-3-[[[(phenylsulfonyl)amino]carbonyl]amino]-1H-indole-2 carboxylic acid; and
18. 4,6 Dichloro 3-[2-[[[(phenylsulfonyl) amino]carbonyl]amino]ethyl]-1H-indole-2-carboxylic acid.

DETAILED DESCRIPTION

The terms in the invention generally have the following meaning.

Loweralkyl means a straight chained or branched chain of from one to four carbon atoms including but not limited to methyl, ethyl, propyl, butyl.

Loweralkenyl means a group from two to four carbon atoms, for example, but not limited to ethylene, 1,2- or 2,3 propylene, 1,2- 2,3-, or 3,4-butylene or isomers thereof.

Loweralkynyl means a group from two to four carbon atoms, for example, but not limited to ethynyl, 2,3 propynyl, 2,3 , or 3,4-butynyl or isomers thereof; propynyl is the preferred group.

Cycloalkyl means a saturated ring of from three to six carbon atoms.

Cycloalkylloweralkyl means cycloalkyl of from three to six carbon atoms and lower alkyl as above, meaning for example, cyclopropylmethyl, cyclobutylmethyl, cyclopentylmethyl, cyclohexylmethyl, and cyclopropylmethyl is the preferred group.

Loweralkoxy means a group of from one to four carbon atoms, for example, but not limited to methoxy, ethoxy, propoxy, butoxy or isomers thereof; methoxy is the preferred group.

Halogen is fluorine, chlorine, bromine, or iodine; fluorine, chlorine and bromine are the preferred groups.

Arylloweralkyl means aryl as defined above and alkyl as defined above, for example, benzyl, 2-phenylethyl, 3 phenylpropyl; preferred groups are benzyl and the benzyl or phenyl is as substituted above.

Arylloweralkenyl means aryl as defined above and alkenyl as defined above, for example, 2-phenyl ethenylenyl, 3-phenylpropenylenyl; preferred groups are 2 phenylethenylenyl and the phenyl is as substituted above.

Monoloweralkylamino means a group containing from one to four carbon atoms, for example, but not limited to methylamino, ethylamino, propylamino or butylamino and isomers thereof.

Diloweralkylamino means a group containing from one to four carbon atoms in each lower alkyl group, for example, but not limited to dimethylamino, diethylamino, di-(n-propyl) amino, di-(n butyl)amino, or may represent a fused ring, for example piperidine.

Heteroaryl means a 5- or 6-membered monocyclic or fused bicyclic; heteroaryl is a monocycle or fused bicyclic aromatic ring containing at least 1 to 4 heteroatoms in one ring if monocyclic or at least one of the ring if fused bicyclic, such as nitrogen, oxygen, or sulfur or a combination thereof, where possible. Such a heteroaryl group includes; for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, thiadiazolyl, benzothiadiazolyl, oxadiazolyl, benzothiazolyl, indolyl, quinolinyl, isoquinolinyl, or N oxides of heteroaryl containing a nitrogen atom. The heteroaryls are generally attached at a ring carbon.

More specifically, such a heteroaryl may be a 2-or 3 thienyl; 2- or 3-furanyl; 2-, or 3 , or 4-pyridyl or pyridyl-N-oxide; 2-, 4-, or 5-pyrimidinyl; 3- or 4-pyridazinyl; 2-pyrazinyl; 2-pyrazinyl-N-oxide; 2- or 3 pyrrolyl; 3-, 4-, or 5-pyrazolyl; 2 , 4-, or 5-oxazolyl; 2-, 4-, or 5-thiazolyl; 3-, 4-, or 5-isoxazolyl; 3 , 4-, or 5-isothiazolyl; 5 tetrazolyl; 3- or 5-(1,2,4,-)triazolyl; 4- or 5-(1,2,3-)triazolyl; 2-, 4-, or 5-imidazolyl; 2-, 3 , 4 , 5 , 6-, or 7-indolyl; 2 , 3-, 4-, 5-, 6 , 7-, or 8-quinolinyl; 1-, 3-, 4-, 5-, 6-, 7-, or 8-isoquinolinyl; 2-, 4-, 5-, 6 , or 7 benzothiazolyl; 2 , 3-, 4-, 5-, 6-, or aryl, or 7 benzothienyl.

Heterocycle means piperidinyl, tetrahydropyridinyl, tetrahydropyranyl, pyrrolidinyl, pyrazolidinyl, oxazolidinyl, tetrahydrofuranyl, tetrahydrothienyl, and the like. The heterocycles are generally attached at a ring carbon.

Amino acid residues means residues of glycine, alanine, isoleucine, leucine, valine, serine, threonine, aspartic acid, glutamic acid, asparagine, glutamine, arginine, lysine, 5 hydroxylysine, cysteine and cystine, methionine, phenylalanine, tyrosine, tryptophan, histidine, proline, or 4-hydroxyproline.

Z is meant to include pharmaceutically acceptable hydrolytically labile groups. Such hydrolytically labile groups are recognized by artisans of ordinary skill to include groups convertible under physiological conditions to a free hydrogen as now defined for Z.

Examples of hydrolytically labile groups and may be esters e.g., the straight chain $C_{1-4}$-alkyl esters, e.g., ethyl; the lower alkanoyloxymethyl esters, e.g., pivaloyloxymethyl; the di-lower alkylamino-straight chain $C_{2-4}$-alkyl esters, e.g., 2-diethylaminoethyl; the pyridylmethyl esters, e.g., 3 pyridylmethyl.

Well known protecting groups and their introduction and removal may be used according to the skill in the art and are described, for example, in J. F. W. McOmie, *Protective Groups in Organic Chemistry*, Plenum Press, London, N.Y. (1973), and T. W. Greene, *Protective Groups in Organic Synthesis*, Wiley, N.Y. (1981).

The compounds of the present invention may contain asymmetric carbon atoms. The instant invention may also include the individual diastereomers and enantiomers, which may be prepared or isolated by methods known to those skilled in the art.

Selected compounds of the present invention can exist also as syn and anti forms and are also the present invention. Selected compounds can also exist as E and Z double bond isomers. Both forms are included in the present invention.

Any resulting racemate can be resolved into the optical antipodes by known methods, for example by separation of the diastereomeric salts thereof, with an optically active acid, and liberating the optically active amine compound by treatment with a base. Racemic compounds of the present invention can thus be resolved into their optical antipodes e.g., by fractional crystallization of d or l-(tartarates, mandelates, or camphorsulfonate) salts.

Additional methods for resolving optical isomers, known to those skilled in the art may be used, for example those discussed by J. Jaques, A. Collet, and S. Wilen in *Enantiomers, Racemates, and Resolutions*, John Wiley and Sons, New York (1981).

Salts of the compounds of the invention are preferably pharmaceutically acceptable salts. The compounds of the invention are acids, acid derivatives, or when possible basic amines. The basic amines may be used to make acid addition salts of pharmaceutically acceptable weak inorganic or organic acids.

The selected compounds of the invention that are acids are also acids from which base salts may be prepared.

The compounds of the instant invention exhibit valuable pharmacological properties by selectively blocking the sensitive excitatory amino acid receptors in mammals. The compounds are thus useful for treating diseases responsive to excitatory amino acid blockade in mammals.

Such disorders include but are not limited to cerebral ischemia or cerebral infarction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma. Other treatments are for schizophrenia, epilepsy, spasticity, neurodegenerative disorders such as Alzheimer,s disease or Huntingtons disease, Olivo-pontocerebellar atrophy, spinal cord injury, and poisoning by exogenous NMDA poisons (e.g., some forms of lathyrism). Further uses include uses as analgesics and anxiolytics.

The effects are demonstrable in in vitro tests or in vivo animal tests using mammals or tissues or enzyme preparations thereof, e.g., mice, rats, or monkeys. The compounds are administered to patients enterally or parenterally, for example, orally, transdermally, subcutaneously, intravenously, or intraperitoneally. Forms include but are not limited to gelatin capsules, or aqueous suspensions or solutions. The applied in vivo dosage may range between about 0.01 to 100 mg/kg, preferably between about 0.05 and 50 mg/kg, most preferably between about 0.1 and 10 mg/kg.

BIOLOGICAL TESTING

Specifically, the compounds of the present invention have activity as antagonists at the strychnine insensitive glycine receptor which is located on the NMDA receptor complex. As such, the compounds of the present invention are NMDA receptor antagonists. Also, the compounds of the present invention have activity as AMPA and kainate receptor antagonists.

For example, compounds of the invention exhibit valuable biological properties because of these excitatory amino acid antagonizing properties. These properties may be ascertained in one or more of the following assays.

The glycine binding assay is performed essentially as described by W. Frost White, et al, *Journal of Neurochemistry* 1989;53(2):503–12.

A selected compound representative of the present invention is shown to be active in the glycine binding assay.

The AMPA binding assay may also be performed to provide an activity profile for the compounds of the present invention.

The kainate binding assay is performed as described by T. Honore et al, *Neuroscience Letters* 1986;65:47-52.

Therefore, the compounds of Formula I and their pharmacologically acceptable salts are effective agents in the prophylaxis and/or therapeutic treatment of disorders responsive to agents which block NMDA receptors, thus forming a further aspect of the present invention in like manner.

Methods of synthesis of the compounds of the instant invention are illustrated in the following schemes. Generally, the preparation of compounds of formula I above wherein $R^5$ is hydrogen and $R^6$ is

wherein $R^1$, $R^2$, $R^3$, $R^4$, $R^8$, and $R^9$ are as defined above are prepared by the method shown in Scheme A.

Scheme A consists of treating a carboxylic acid of the general structure A or B with diphenylphosphorylazide in the presence of a trialkylamine base; a weak or other nonnucleophilic base in an inert solvent to produce an isocyanate of general structure C or D. Alternatively, the carboxylic acid may be treated with a coupling reagent to produce an activated carboxylic acid derivative. The resulting activated acid is reacted with sodium azide or potassium azide to produce the isocyanate of general formula C or D. Suitable coupling agents for this purpose include, for example, such reagents as thionyl chloride, carbonyl diimidazole and DCC, preferably thionyl chloride. By "activated carboxylic acid derivative" is meant an acid derivative which is capable of reacting with sodium azide or potassium azide. By inert solvent is meant a nonprotic solvent, such as for example, methylene chloride, chloroform, toluene, benzene, tetrahydrofuran, or the like. The isocyanates C or D are then reacted with a variety of nitrogen nucleophiles to produce ureas E or F wherein A, $R^1$, $R^2$, $R^3$, $R^4$, Z, $R^8$, and $R^9$ are as defined above. The compounds of general formula E or F may be treated with hydroxide ion to afford the compounds of Formula I wherein Y is OH.

Alternatively, as shown in Scheme B, the compounds of general formula C or D may be reacted with a variety of oxygen nucleophiles to produce carbonates of the general formula i or J. Treatment with hydroxide ion provided the compounds of Formula I.

The compounds of general formula i or J (Scheme C) wherein $R^8$ is tert-butyl may be further reacted by treatment with an acid to provide the compounds of general formula M or N. Compounds M or N may be treated with a variety of electrophiles to provide compounds of formula O or P wherein $R^1$, $R^2$, $R^3$, $R^4$, H, $R^5$, $R^6$, q, and p are as previously defined. As in previous examples, the compounds of general formula O or P may be optionally further treated by conventional methods to obtain the compounds of Formula I wherein Y is OH.

Further, preparation of compounds of the Formula I wherein A is $(CH_2)_n$ and n is O and $R^1$, $R^2$, $R^3$, $R^4$, Z, and $R^8$ are as previously defined are illustrated in Scheme D. Treatment of the compounds of the general structure with sodium nitrite in tetrahydrofuran containing acetic acid may provide the compounds of general structure B'. Reduction of the compounds of formula B' with hydrogen and Raney Nickel or by other methods known to those skilled in the art may provide the compounds of the general structure C'. The compounds of the general structure C' may be converted to the compounds of Formula I as illustrated in Scheme C.

Further, the preparation of the compounds of Formula I wherein $R^5$ and $R^6$ are taken together with the nitrogen to form

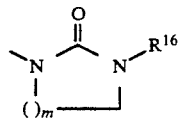

wherein $R^{16}$ is as previously defined and m is one or two and $R^1$, $R^2$, $R^3$, $R^4$, and Z are as previously defined is illustrated in Scheme E.

The compounds of the general formula C' or D'' are treated with $R^{16}NHCH_2(CH_2)_mOH$ in the presence of potassium carbonate or sodium carbonate and diethyl carbonate or dimethyl carbonate is heated at a temperature between 100° to 130° C. to provide the compounds of general formula E' or E''. Treatment of the compounds of the general structure E' or E'' with sodium hydroxide, potassium hydroxide, or lithium hydroxide provided the compounds of Formula I.

SCHEME A

-continued
SCHEME A
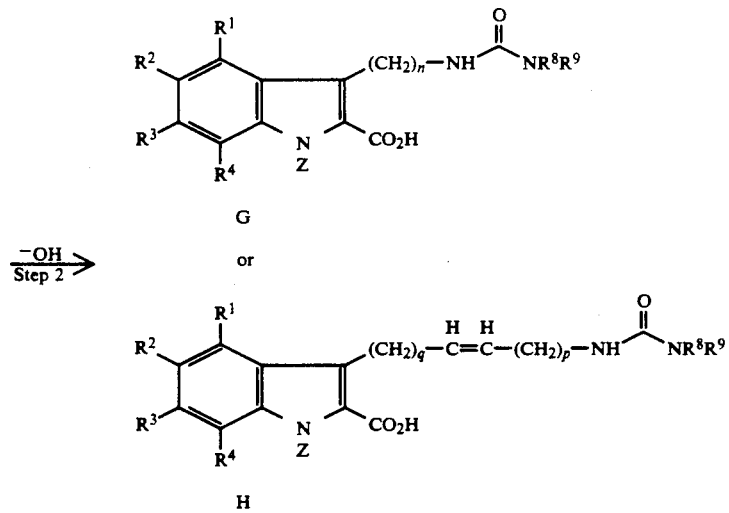
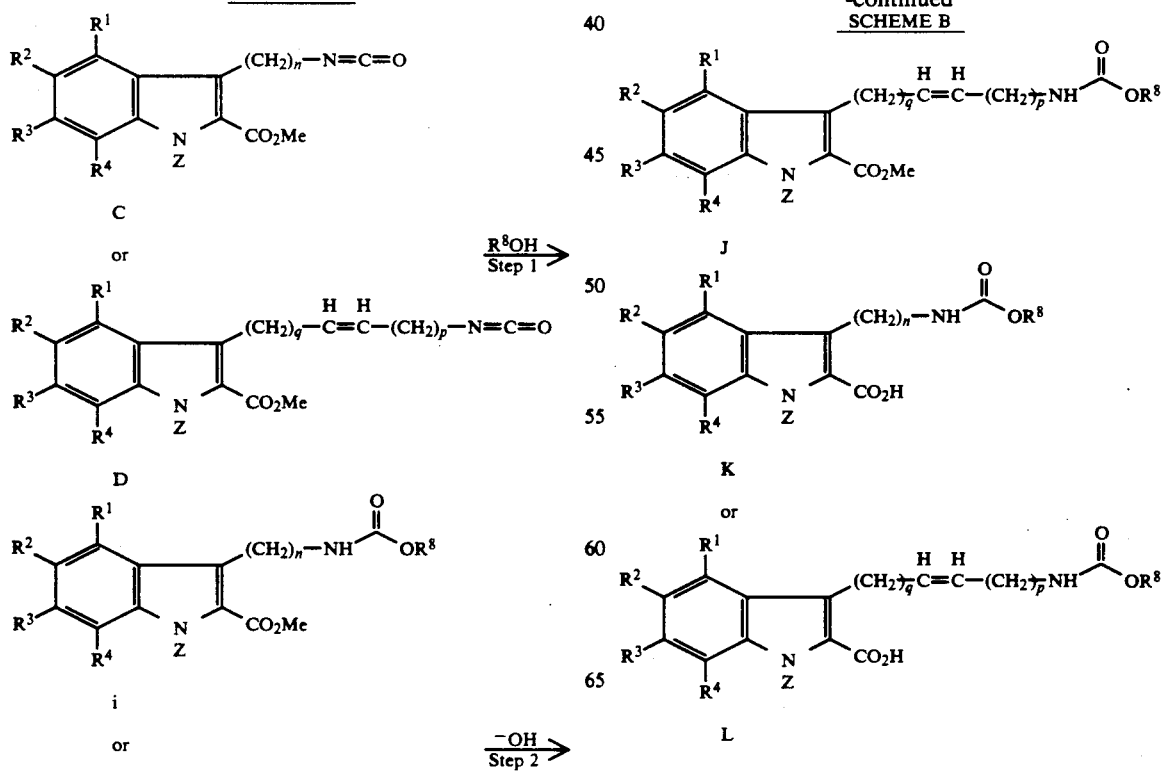

SCHEME C
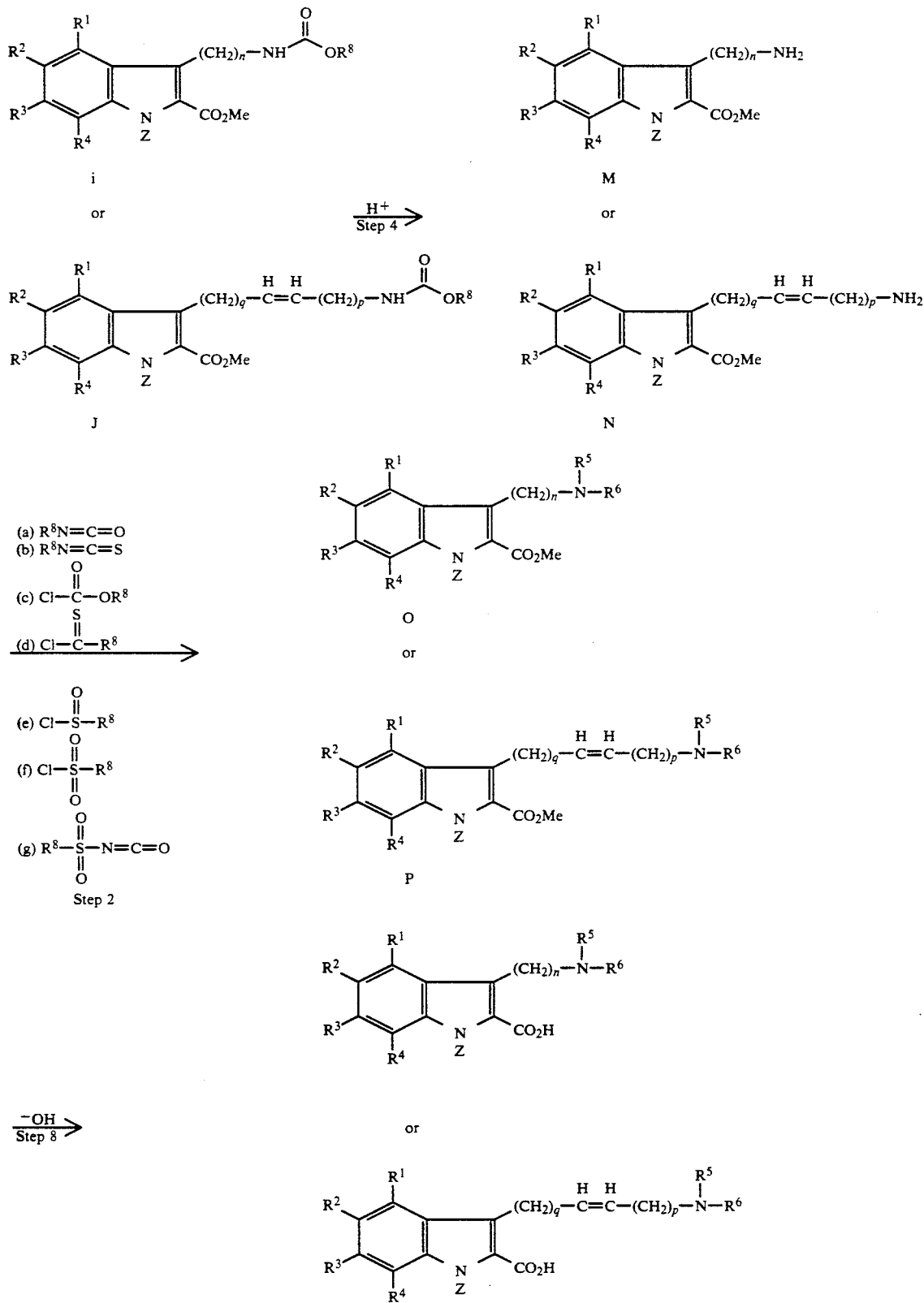

SCHEME D
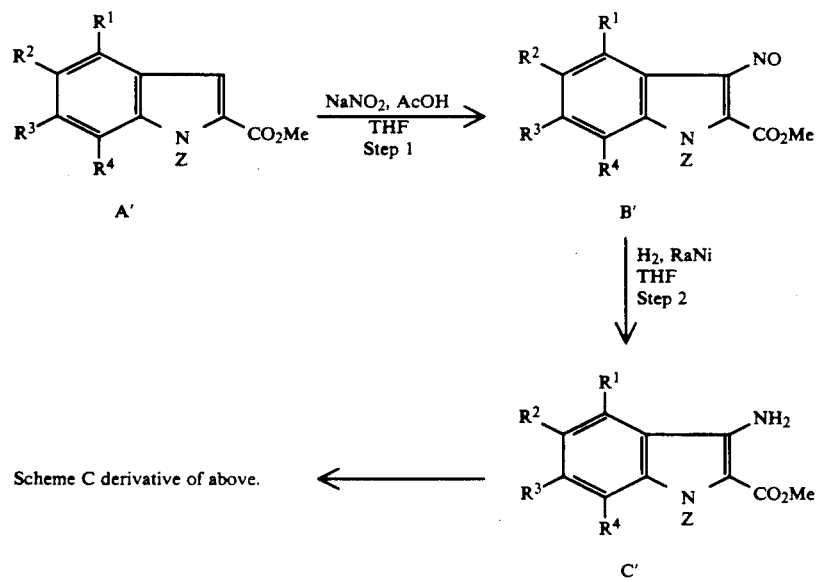
Scheme C derivative of above.
SCHEME E
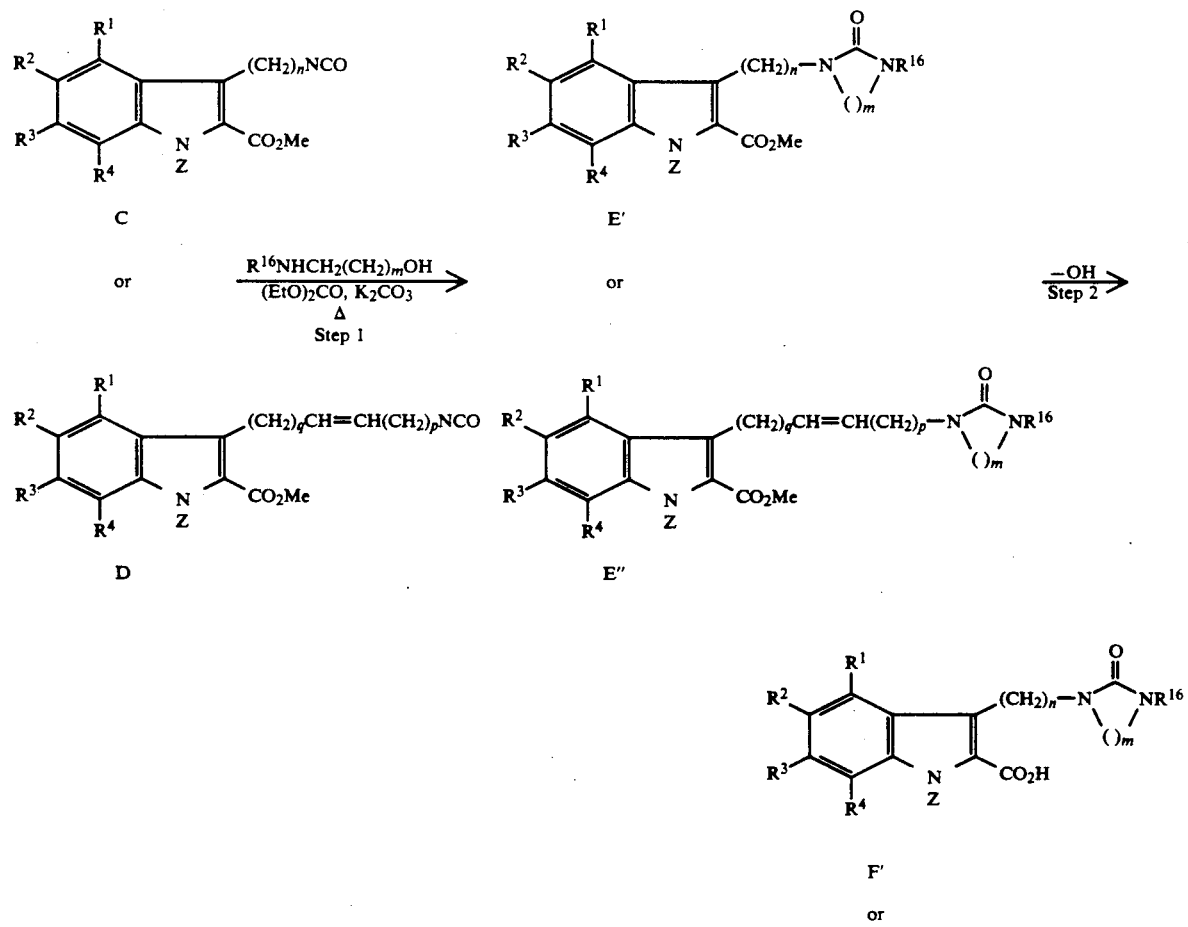

-continued
SCHEME E

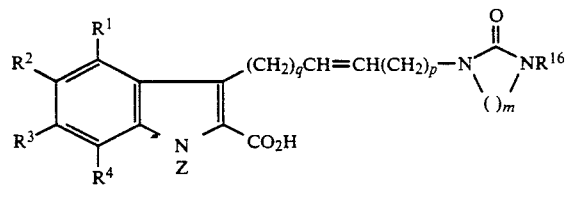

F"

Pharmaceutically acceptable salts of the compounds of Formula I or II are also included as a part of the present invention.

The base salts may be generated from compounds of Formula I or II by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, *J. Pharm. Sci.* 1977;66:1-19.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

Starting materials for the processes described above are known or can be prepared by known processes.

The products of the reactions described herein are isolated by conventional means such as extraction, distillation, chromatography, and the like.

Variations within the processes described are within the skill of the art for the preparation of compounds of the Formula I.

PHARMACEUTICAL COMPOSITIONS

The compounds of the present invention can be administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For example, parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1,000 mg preferably 10 mg to 100 mg according to the particular application and the potency of the active component. The composition can, if desired, also contain other compatible therapeutic agents.

METHOD OF TREATING

The compounds of this invention are useful in the treatment of central nervous system disorders related to their biological activity. The compounds of this invention may accordingly be administered to a subject, including a human, in need of treatment, alleviation, or elimination of an indication associated with the biological activity of the compounds as set out above. This includes especially excitatory amino acid dependent psychosis, excitatory amino acid dependent anorexia, excitatory amino acid dependent ischemia, excitatory amino acid dependent convulsions, and excitatory amino acid dependent migraine. Suitable dosage ranges are 0.1 to 1,000 mg daily, 10 to 400 mg daily, and especially 30 to 100 mg daily, dependent as usual upon the exact mode of administration, form in which administered, the indication toward which the administration is directed, the subject involved and the body weight of the subject involved, and further, the preference and experience of the physician in charge.

The following nonlimiting example illustrates the synthesis of several compounds within the present invention. More specifically, the following preparations and examples illustrate the present invention.

PREPARATION 1

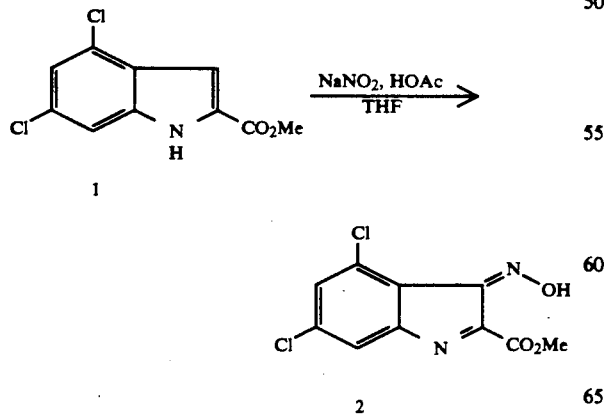

Ref: Huang, H.; Mann, F. G. J. Chem. Soc. 1949; 2903.

To a solution of the indole 1 (2.6 g, 10.65 mmol) in 40 mL of THF and 50 mL of acetic acid at room temperature under argon atmosphere was added solid sodium nitrite (4.5 g, 65.22 mmol) slowly in small portions. The reaction mixture was allowed to stir at room temperature overnight and then quenched by addition of water (100 mL). The yellow precipitates were collected and washed with water. It was then air dried to give the oxime 2 as a yellow solid: $^1$H NMR (DMSO-$d_6$, 200 NHz) d 7.99 (d, 1H, J=1.7 Hz), 7.63 (d, 1H, J=1.7 Hz), 3.95 (s, 3H), 3.90 (s, 1H).

PREPARATION 2

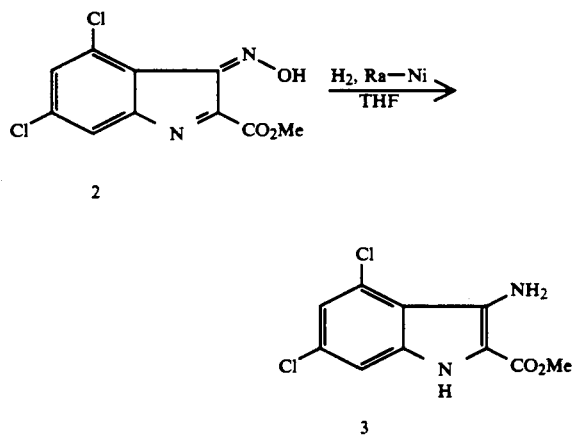

Raney nickel is added to a solution of the oxime 2 in THF. The reaction mixture is stirred under hydrogen at 1 atmosphere to give the amine 3.

PREPARATION 3

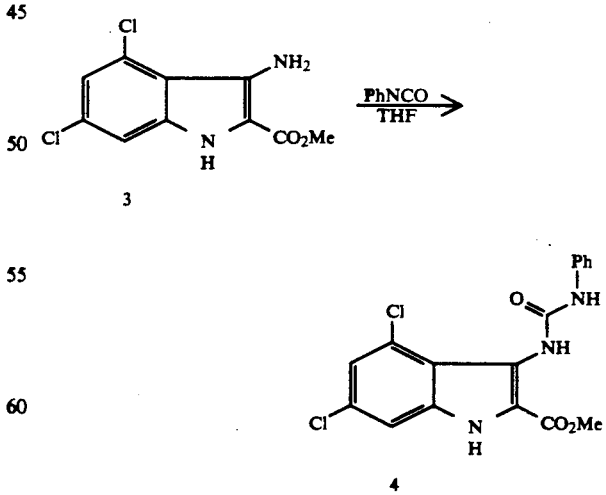

Phenyl isocyanate is added to a solution of the amine 3 in THF at 0° C. The reaction mixture is then stirred at room temperature to give the urea 4.

EXAMPLE 1

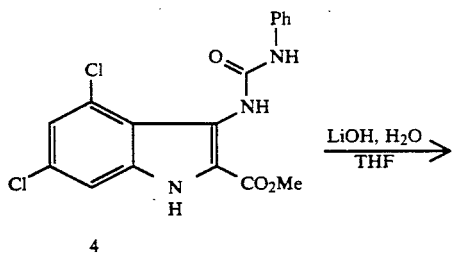

A solution of 1M lithium hydroxide in water (4 equiv) is added to a solution of the ester 4 (1 equiv) at room temperature. The reaction mixture is then stirred overnight and excess solvent is removed. Water is added to redissolve the residue and then conc. HCl is added at 0° C. to generate the acid 5.

PREPARATION 4

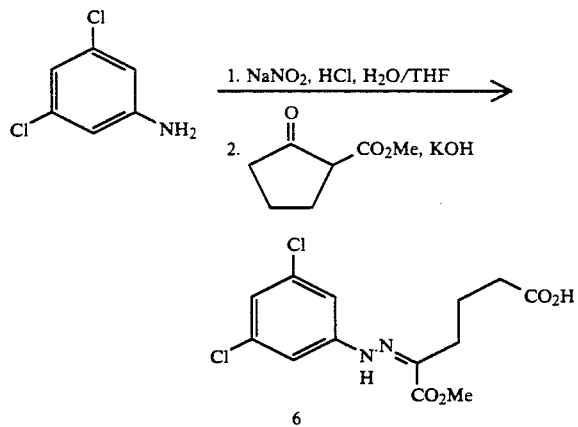

To a solution of concentrated hydrochloric acid (23 mL, 0.28 mol) in 90 mL of water at −5° C. is added a solution of 3,5 dichloroaniline (15.0 g, 93 mmol) in 10 mL THF. The reaction mixture is allowed to stir at −5° C. for 20 minutes and a solution of sodium nitrite (6.4 g, 93 mmol) in 20 mL of water is added slowly. The reaction mixture is kept below 0° C. with stirring until most of the solid went into solution (ca 30 minutes), the diazonium salt solution is then kept at 0° C. for further use. A potassium hydroxide 16.3 g, 0.29 mol) in 120 mL is prepared and cooled to 0° C. Methyl 2-oxocyclopentanecarboxylate (12.9 g, 91 mmol) is placed in a separatory funnel and was shaken vigorously with 60 mL of the KOH solution. Benzene 15 mL) is then added to extract out the unreacted cyclopentanone. The aqueous layer is collected and the benzene layer is reextracted with the remaining potassium hydroxide solution. The aqueous layers are poured onto 150 g of ice followed by the addition of the diazonium salt solution. The solid formed is collected and dissolved in 500 mL of chloroform. The chloroform solution is washed once with brine and dried with magnesium sulphate. The solid product obtained after filtration and concentration is triturated with ether-hexane mixture. The yellow solid is then collected by filtration and air dried: $^1$H NMR (DMSO-d$_6$, 200 MHz) δ 12.25 (s, 1H), 10.28 (s, 1H), 7.23 (d, 2H, J=1.81 Hz), 7.07 (t, 1H, J=1.81 Hz), 3.76 (s, 3H), 2.59 (t, 2H), J=8.12 Hz), 2.30 (t, 2H, J=7.27 Hz), 1.65 (m, 2H).

PREPARATION 5

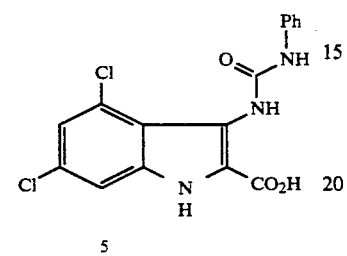

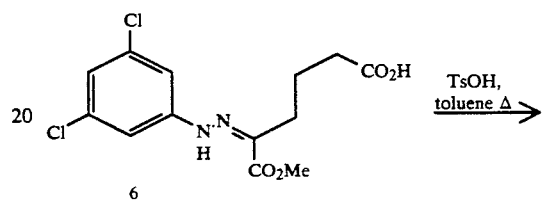

A solution of p-toluenesulfonic acid monohydrate (0.36 g, 1.89 mmol) in 25 mL of toluene is refluxed under azeotropic conditions for 1 hour to remove water. The solution is cooled to room temperature and the hydrazone 6 (0.32 g, 0.95 mmol) is added. The resulting mixture was refluxed for 3 hours and then cooled to 0° C. Saturated sodium carbonate solution (20 mL) and water (10 mL) are added to quench the reaction. The aqueous layer is collected and washed once with ethyl acetate and then cooled to 0° C. followed by acidification with concentrated hydrochloric acid to pH 1. The precipitates are collected by filtration and washed with water (4x). The indole carboxylic acid 7 (0.18 g, 60%) is obtained as an off-white powder after being air-dried overnight: $^1$H NMR (DMSO-d$_6$, 200 MHz) δ12.17 (s, 2H), 7.42 (d, 1H, J=1.7 Hz), 7.20 (d, 1H, J=1.7 Hz), 3.90 (s, 3H), 3.50 (dd, 2H, J=8.1, 6.0 Hz), 2.46 (m, 2H, partly buried under DMSO signal).

PREPARATION 6

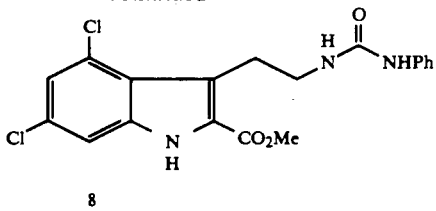

8

A solution of the acid 7 (2.00 g, 6.33 mmol) and triethylamine (0.88 mL, 6.33 mmol) in 50 mL of toluene was treated with diphenylphosphorylazide (1.27 mL, 6.33 mmol) and the resulting solution heated to reflux for 30 minutes. The reaction mixture was treated with aniline (0.59 g, 6.33 mmol) and heated at reflux for 1 hour. The reaction mixture was cooled to room temperature and ethyl acetate (100 mL) was added. The resulting solution was washed with H$_2$O (30 mL), dried MgSO$_4$, filtered, and concentrated. The residue was suspended in 1:1 heptane/ethyl acetate and the solid collected by suction filtration. A white solid was obtained (0.81 g, 32%).

EXAMPLE 7

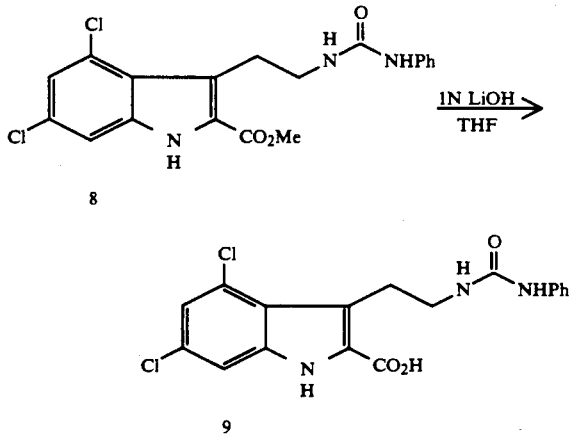

A solution of the ester 8 (0.48 g, 1.18 mmol) in 20 μL of THF was treated dropwise with aqueous 1N LiOH. The resulting solution was stirred at room temperature for ~8 hours and acidified with 1N HCl. The solid which formed was collected by suction filtration, washed with ether, and dried under vacuum to give the product 9 as a white solid (0.31 g, 67%).

We claim:

1. A compound of the formula

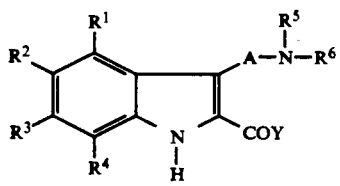

or a pharmaceutically acceptable base or acid addition salt thereof; wherein
(1) Y is (a) OH; (b) OR$_{30}$ wherein R$_{30}$ is lower alkyl, phenyl, phenylalkyl wherein the alkyl is an alkylene of from one to four carbons and the phenyl is unsubstituted or substituted by from one to three substituents selected from lower alkyl, halogen, trifluoromethyl, nitro, amino, mono- or di-lower alkylamino, hydroxy, lower alkoxy, C(O)OH, and NHCOR$^5$ wherein R$^5$ is lower alkyl, lower alkenyl, phenyl, phenylloweralkyl, phenylloweralkenyl or where the phenyl is substituted as defined above; (c) NR$_{40}$R$_{50}$ wherein R$_{40}$ and R$_{50}$ are independently hydrogen or lower alkyl; or (d) OCH$_2$OR$_{30}$ wherein R$_{30}$ is as defined above;
(2) R$^1$, R$^2$, R$^3$, and R$^4$ are independently hydrogen, lower alkyl, halogen, trifluoromethyl, cyano, nitro, methylthio, lower alkenyl, lower alkynyl, SO$_2$NH$_2$, S(O)$_{1-2}$R wherein R is hydrogen or lower alkyl, OCF$_3$;
(3) A is —(CH$_2$)$_n$—, —(CH$_2$)$_q$CH=CH(CH$_2$)$_p$—,

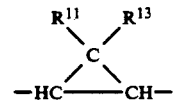

wherein R$^{11}$ and R$^{13}$ are independently as defined below and n is an integer of 0 through 4, q is an integer of 0 or 1, p is an integer of 1 or 2;
(4) R$^5$ is hydrogen, alkyl of from one to twenty carbons, phenyl or phenyl substituted as defined above;
(5) R$^6$ is
 (a) CONR$^8$R$^9$,
 (b) COOR$^8$,
 (c) CSR$^8$,
 (d) S(O)$_{1-2}$R$^8$,
 (e) S(O)$_{1-2}$NR$^8$R$^9$, or
 (f) CONR$^8$S(O)$_{1-2}$R$^9$, wherein R$^8$ and R$^9$ are independently
(i) hydrogen; (ii) alkyl of from one to twenty carbons, or alkenyl of from one to twenty carbons; (iii) (C$_3$-C$_6$) cycloalkyl or (C$_3$-C$_6$) cycloalkylloweralkyl; (iv) phenyl or phenyl substituted by one to three of lower alkyl, halogen, trifluoromethyl, nitro, amino, mono- or di-lower alkylamino, hydroxy, lower alkoxy, C(O)OH, NHCOR$^{10}$ wherein R$^{10}$ is lower alkyl, lower alkenyl, phenyl, phenylloweralkyl, phenylloweralkenyl, or where the phenyl is substituted as defined above, NHSO$_2$R$^{10}$ wherein R$^{10}$ is as defined above, CN, CONR$^{10}$R$^{11}$ wherein R$^{10}$ is as defined above and R$^{11}$ is hydrogen or lower alkyl, or S(O)$_{0-2}$R$^{10}$ wherein R$^{10}$ is as defined herein; (v) phenylloweralkyl or where the phenyl is substituted as defined above; (vi) phenylloweralkenyl or where the phenyl is substituted as defined above; (vii) (CH$_2$)$_q$R$^{12}$ wherein q is an integer of one to four and R$^{12}$ is (A) SO$_3$R$^{13}$ wherein R$^{13}$ is hydrogen or lower alkyl, (B) PO$_3$R$^{13}$ wherein R$^{13}$ is as defined above, (C) CO$_2$R$^{13}$ wherein R$^{13}$ is as defined above, or (D) NR$^{14}$R$^{15}$ wherein R$^{14}$ and R$^{15}$ are independently hydrogen or alkyl; or
(6) R$^5$ and R$^6$ are taken together with N which form

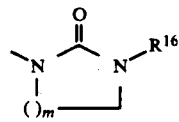

wherein m is an integer one or two and $R^{16}$ is lower alkyl, phenyl, phenylloweralkyl or where the phenyl is substituted as defined above.

2. A compound of claim 1 wherein Y is OH.
3. A compound of claim 1 wherein A is $-(CH_2)_n-$.
4. A compound of claim 1 wherein A is $-CH=CH(CH_2)_{1-2}$.
5. A compound of claim 1 wherein A is $-CH_2CH=CHCH_2-$.
6. A compound of claim 1 wherein A is

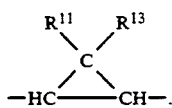

7. A compound of claim 1 wherein $R^6$ is $CONR^8R^9$.
8. A compound of claim 1 wherein $R^6$ is $COOR^8$.
9. A compound of claim 1 wherein $R^6$ is $CSR^8$.
10. A compound of claim 1 wherein $R^6$ is $S(O)_{1-2}R^8$.
11. A compound of claim 1 wherein $R^6$ is $S(O)_{1-2}NR^8R^9$.
12. A compound of claim 1 wherein $R^6$ is $CONR^8S(O)_{1-2}R^9$.
13. A compound of claim 1 wherein $R^5$ and $R^6$ together with the N are

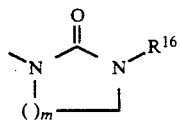

14. A compound of claim 1 which is
(1) Methyl 4,6-dichloro-3-[2-[[(phenylamino)carbonyl]amino]ethyl]-1H-indole-2-carboxylate;
(2) Methyl 4,6 dichloro 3-[2 [[[(phenylmethyl)amino]carbonyl]amino]ethyl]-1H-indole-2-carboxylate;
(3) Methyl 4,6-dichloro-3-[2-[[[(3,5-dichlorophenyl)amino]carbonyl]amino]ethyl]-1H -indole-2-carboxylate;
(4) Methyl 4,6-dichloro 3-[2 [[[(2-methylphenylamino]carbonyl]amino]ethyl]-1H -indole-2 carboxylate;
(5) Methyl 4,6-dichloro-3-[2-(2-oxo-3-phenyl 1-imidazolidinyl)ethyl]-1H-indole-2carboxylate;
(6) 4,6-Dichloro-3 [2-[[(phenylamino)carbonyl]amino]ethyl]-1H-indole-2-carboxylic acid;
(7) 4,6-Dichloro-3-[2-[[[(phenylmethyl)amino]carbonyl]amino]ethyl]-1H-indole-2-carboxylic acid;
(8) 4,6-Dichloro-3-[2 [[[(3,5-dichlorophenyl)amino]carbonyl]amino]ethyl]-1H -indole-2-carboxylic acid;
(9) 4,6-Dichloro-3-[2 [[[(2-methylphenyl)amino]carbonyl]amino]ethyl]-1H-indole-2-carboxylic acid;
(10) 4,6-Dichloro-3 [2 (2 oxo-3 phenyl 1-imidazolidinyl)ethyl]-1H indole-2-carboxylic acid;
(11) 4,6-Dichloro-3-[[(phenylamino)carbonyl]amino]-1H indole 2 carboxylic acid;
(12) 4,6-Dichloro-3 [[[(phenylamino)carbonyl]amino]methyl]-1H-indole-2-carboxylic acid;
(13) 4,6-Dichloro-3-[3-[[(phenylamino)carbonyl]amino]propyl]-1H-indole 2 carboxylic acid;
(14) 4,6-Dichloro-3-[3-(2-oxo-3-phenyl-1-imidazolidinyl)propyl]-1H-indole-2-carboxylic acid;
(15) 4,6-Dichloro 3-[(2-oxo-3-phenyl-1-imidazolidinyl)methyl]-1H-indole-2-carboxylic acid;
(16) 4,6-Dichloro-3-(2-oxo-3-phenyl-1-imidazolidinyl)-1H-indole-2-carboxylic acid;
(17) 4,6-Dichloro-3-[[[(phenylsulfonyl)amino]carbonyl]amino]-1H-indole-2-carboxylic acid; and
(18) 4,6-Dichloro-3-[2-[[[(phenylsulfonyl)amino]carbonyl]amino]ethyl]-1H-indole-2-carboxylic acid.

15. A pharmaceutical composition comprising a therapeutically effective amount of a compound of the Formula I of claim 1 together with a pharmaceutically acceptable carrier.

16. A method for treating disorders responsive to the blockade of glutamic and aspartic acid receptors comprising administration to a patient in need thereof an effective amount of a compound of Formula I of claim 1 in unit dosage form.

* * * * *